US006599448B1

(12) United States Patent
Ehrhard, Jr. et al.

(10) Patent No.: US 6,599,448 B1
(45) Date of Patent: Jul. 29, 2003

(54) RADIO-OPAQUE POLYMERIC COMPOSITIONS

(75) Inventors: Joseph A. Ehrhard, Jr., Flemington, NJ (US); Patrick Hennessey, Fords, NJ (US)

(73) Assignee: Hydromer, Inc., Branchburg, NJ (US)

( * ) Notice: Subject to any disclaimer, the term of this patent is extended or adjusted under 35 U.S.C. 154(b) by 0 days.

(21) Appl. No.: 09/568,115

(22) Filed: May 10, 2000

(51) Int. Cl.[7] .................. A61K 49/04; G01N 31/00
(52) U.S. Cl. ................ 252/582; 424/9.4; 424/9.43; 424/9.45; 424/9.451; 252/408.1; 252/583
(58) Field of Search ............. 424/9.45, 9.451, 424/9.4, 9.43; 252/582, 408.1, 583

(56) References Cited

U.S. PATENT DOCUMENTS 4,406,878 A * 9/1983 DeBoer ............... 424/9.451
4,866,132 A * 9/1989 Obligin et al. .......... 424/9.45
5,342,605 A * 8/1994 Illig ................... 424/9.451
5,525,327 A * 6/1996 Baker et al. ........... 424/9.45
5,567,410 A * 10/1996 Torchilin et al. ........ 424/9.45
5,746,998 A * 5/1998 Torchilin et al. ........ 424/9.45
6,040,408 A * 3/2000 Koole ................. 424/9.45
6,426,145 B1 * 7/2002 Moroni ................. 424/9.4

FOREIGN PATENT DOCUMENTS

WO          82/01006        *     4/1982

* cited by examiner

Primary Examiner—Philip Tucker
(74) Attorney, Agent, or Firm—Hoffmann & Baron, LLP

(57) ABSTRACT

The present invention provides a radio-opaque composition including a polymer or monomer, wherein the polymer or monomer has a non-leachable radio-opaque moiety. The non-leachable radio-opaque moiety is covalently attached to the polymer or monomer.

40 Claims, No Drawings

RADIO-OPAQUE POLYMERIC COMPOSITIONS

BACKGROUND OF THE INVENTION

The invention relates to radio-opaque polymeric compositions which can be used as covering compositions for polymeric, ceramic and metal objects. Additionally, this invention relates to radio-opaque objects and methods for rendering objects radio-opaque.

The ability to render objects radio-opaque is important in several fields. It is especially important in the medical field. For example, medical devices which are radio-opaque enable easy radiological localization of such devices during medical procedures and post-operative follow-ups. In the industrial field there are many applications in which it is important to render devices radio-opaque in order to enable differentiation or to shield objects from X-rays.

Current methods of rendering objects radio-opaque involve compounding materials like barium sulfate (i.e., BaSO$_4$) into the objects; or plating/ion sputtering silver or gold onto the objects. It also is conventional for many medical device polymers to be filled with barium or bismuth radio-opaque compounds. Recently, radio-opaque paints and inks with barium sulfate or silver powders physically trapped in the composition have been proposed. Lead is also used in non-medical applications, typically in plated form or compounded into ceramics.

There are several disadvantages with the current methods of rendering objects radio-opaque. In particular, medical devices treated with the current methods have low biocompatibility and may be toxic to tissues. Additionally, when the ion deposition is used on stents, the likelihood of restenosis increases. Other disadvantages with the current methods in the medical and the industrial fields include toxicity, galvanic corrosion, high economic cost, undesirable changes in the physical and electromagnetic properties of the devices and cumbersome processes in producing the devices. Additionally, current methods of shielding objects from X-rays are impractical and expensive.

Accordingly, it is one of the purposes of this invention, among others, to provide coverings and primers which will render objects radio-opaque without the disadvantages found in the prior art.

SUMMARY OF THE INVENTION

The present invention provides a radio-opaque composition including a polymer or monomer, wherein the polymer or monomer has a non-leachable radio-opaque moiety. The non-leachable radio-opaque moiety is covalently attached to the polymer or monomer.

Examples of a radio-opaque moiety include a halogenated aromatic compound with an attached reactive functional group. Examples of halogenated aromatic compounds include aromatic tri-iodides, aromatic tri-bromides, aromatic tri-fluorides and aromatic tri-chlorides. Examples of attached reactive functional groups include a hydroxyl, a carboxyl, an amine, an amide, a carbonyl, a thiol, an allyl, a vinyl or an anhydride group.

Further examples of the radio-opaque moiety include an amidotrizoate, an iothalamate, an iohexol, an iopamidol, an iopromide, ioxaglic acid, an iopadate, an iotroxate or an ioxaglate. Further examples of the radio-opaque moiety include Iobenguane, Iobenzamic Acid, Iocarmic Acid, Iocetamic Acid, Iodamide, Iodipamide, Iodixanol, Iodized Oil, Iodoalphionic Acid, p-Iodoaniline, o-Iodobenzoic Acid, lodochlorhydroxyquin, o-Iodohippurate Sodium, o-Iodophenol, p-Iodophenol, Iodophthalein Sodium, Iodopsin, Iodopyracet, Iodopyrrole, Iodoquinol, Iofetamine $^{123}$I, Ioglycamic Acid, Iohexol, Iomeglamic Acid, Iopamidol, Iopanoic acid, Iopentol, Iophendylate, Iophenoxic Acid, Iopromide, Iopronic Acid, Iopydol, Iopydone, Iothalamic Acid, Iotrolan, Ioversol, Ioxaglic Acid, Ioxilan, or Ipodate.

The polymer or monomer preferably has at least one reactive functional group. Examples of reactive functional groups are an isocyanate, an isothiocyanate, an ester, an aldehyde, an N-hydroxysuccinimide ester, an epoxide, a carboxylic ester, a tresylate, an anhydride, an alkyl halide, a carboxylic acid, a haloketone, an alkene, an alkyne or an acyl chloride.

In one embodiment the polymer is a synthetic polymer. The synthetic polymer can be a polymer blend, alloy, homopolymer, random copolymer, block copolymer or graft copolymer. The polymer blend, alloy, random copolymer, block copolymer or graft copolymer includes poly(vinyl alcohol), poly(vinylpyrrolidone), poly(caprolactone), poly(hydroxybutarates), poly(caprolactams), poly(acrylamides), poly(terephthalate), poly(vinyl chloride), poly(propylene), poly(ethylene oxide), poly(acrylic acid), poly(propylene oxide), poly(styrene), poly(ethylene), poly(urethanes), silicone elastomers or combinations thereof. The polymer can be a homopolymer of the aforementioned polymers.

In another embodiment the polymer is a natural polymer. Examples of a natural polymer include a cellulose, chitosan, chitin, starch, hyaluronic acid, chondroitin sulfate, zanthan, guar gum; or an ether or an ester derivative thereof; or a block, a graft or random copolymer thereof; or a blend thereof.

Examples of the monomers of the present invention include an acrylate, allyllic compound, amide, amine, anhydride, epoxide, isocyanate, methacrylate, silyl, thiol compound, thioisocyanate, vinyl compound, ester, acid chloride, acrolein or acryloylchoride.

Examples of the covalent attachment between the radio-opaque moiety and the polymer or monomer include an alkyl, amine, amide, anhydride, azide, carbamate, carbonate, carboxyl, ether, ester, imide, thiol, thiocarbamates, thioisocyante, urea or other covalent linkage.

In one embodiment the radio-opaque moiety can be covalently attached to the polymer or monomer by the use of heat, ultraviolet irradiation, gamma irradiation, an acidic initiator, a basic initiator, a peroxide initiator, a persulfate initiator or an azo initiator.

In one embodiment the composition of the present invention can further include at least one additional ingredient wherein the additional ingredient is releasable or non-releasable from the composition. In one embodiment the additional ingredient is a biologically active material. Examples of the biologically active material include a biostatic agent, a cytostatic agent, a radiation emitter, a biomolecule, an anti-inflammatory agent, an immunosuppressant or an antiseptic. Preferred biologically active materials include antibiotics and antithrombotic agents.

In one embodiment the composition has a low coefficient of friction when wetted with water or a water-containing substance. In this embodiment the composition can include a polyvinylpyrrolidone-polyurethane complex.

In one embodiment the composition can further include a solvent. The covalent linkage between the polymer or monomer and the radio-opaque moiety can be formed as the solvent is removed. Alternately, the covalent linkage can be formed during formulation of the composition.

In one embodiment the composition is a covering composition. Examples of covering compositions include coatings and primers. The primers of the present invention can be made of the same monomer or of a blend of monomers. The primers can include monomers which are covalently attached to an object by a covalent linkage; or they can include monomers which adhere to an object.

The present invention includes radio-opaque objects. In one embodiment the material of which the radio-opaque object is composed includes the composition of the present invention. In another embodiment the object is covered with a composition. The object can be a medical device. Examples of medical devices include catheters, guide wires, shunts, screws, pins, prostheses, plates, films, sponges, sutures, tubes, cannulas, balloons, needles, markers or stylets. A preferred medical device is a stent.

The present invention includes a method of rendering an object radio-opaque. In one embodiment the method includes: applying a covering composition to the object, wherein the covering composition includes a polymer or monomer. The polymer or monomer has a non-leachable radio-opaque moiety. The method can further include: placing the covering composition in a solvent, applying the covering composition in the solvent to the object and evaporating the solvent. Examples of application of the covering composition include spraying, dipping, plasma vapor deposition, flow coating, brushing or dabbing.

The present invention provides radio-opaque compositions and objects which avoid the disadvantages of current methods used to render objects radio-opaque. In particular, the present invention provides compositions that are biocompatible; unlike medical devices treated with current methods which have low bio-compatibility and may be toxic to tissues. Additionally, the present invention avoids the increased likelihood of restenosis associated with current methods of ion deposition of stents. The present invention also avoids the problems associated with the current methods in the medical and the industrial fields including toxicity, galvanic corrosion, high economic cost, undesirable changes in the physical and electromagnetic properties of the devices and cumbersome processes in producing the devices. These and other advantages of the present invention will be appreciated from the detailed description and examples which are set forth herein. The detailed description and examples enhance the understanding of the invention, but are not intended to limit the scope of the invention.

DETAILED DESCRIPTION OF THE PREFERRED EMBODIMENTS

The present invention provides radio-opaque compositions. The radio-opaque compositions include a monomer or a polymer wherein the monomer or the polymer has at least one radio-opaque moiety. The radio-opaque moiety is covalently attached to the monomer or polymer and is non-leachable (i.e., the radio-opaque moiety is inhibited from leaching into surrounding media).

The radio-opaque moiety of the present invention is any compound or molecule which imparts radio-opacity and which can be attached to a monomer or polymer. For example, a radio-opaque moiety can be a halogenated aromatic compound with at least one attached reactive functional group. Examples of a halogenated aromatic compound include, but are not limited to, aromatic tri-iodides, aromatic tri-bromides, aromatic tri-chlorides and aromatic tri-fluorides. The attached reactive functional group is any functional group that enables the radio-opaque moiety to be attached to the monomer or the polymer of the present invention. Examples of the attached reactive functional groups include, but are not limited to, hydroxyls, carboxyls, amines, amides, carbonyls, thiols, allyls, vinyls and anhydrides. Preferred examples of the radio-opaque moiety to be used in the present invention can include, but are not limited to, amidotrizoates, iothalamates, iohexols, iopamidols, iopromides, ioxaglic acids, iopadates, iotroxates and ioxaglates. Preferred examples of the radio-opaque moiety to be used in the present invention can be found, for example, in the $12^{th}$ Edition of the Merck Index published by Merck & Co., Whitehouse Station, N.J. pages 859–869 and include, for example, iobenguane, iobenzamic acid, iocarmic acid, iocetamic acid, iodamide, iodipamide, iodixanol, iodized oil, iodoalphionic acid, p-iodoaniline, o-iodobenzoic acid, iodochlorhydroxyquin, o-iodohippurate sodium, o-iodophenol, p-iodophenol, iodophthalein sodium, iodopsin, iodopyracet, iodopyrrole, iodoquinol, iofetamine $^{123}$I, ioglycamic acid, iohexol, iomeglamic acid, iopamidol, iopanoic acid, iopentol, iophendylate, iophenoxic acid, iopromide, iopronic acid, iopydol, iopydone, iothalamic acid, iotrolan, ioversol, ioxaglic acid, ioxilan and ipodate.

The polymers and monomers of the present invention are monomers or polymers to which at least one non-leachable radio-opaque moiety can be attached and which have at least one reactive functional group. The preferred reactive functional groups to be used in the present invention include, but are not limited to, isocyanates, isothiocyanates, esters, aldehydes, N-hydroxysuccinimide esters, epoxides, carboxylic esters, tresylates, anhydrides, alkyl halides, carboxylic acids, haloketones, alkenes, alkynes or acyl chlorides. Especially preferred are polymers and monmers with at least one reactive isocyanate group.

The polymers of the present invention can be synthetic or natural.

Preferred synthetic polymers utilized in the present invention include, but are not limited to, poly(vinyl alcohol), poly(vinylpyrrolidone), poly(caprolactone), poly(hydroxybutarates), poly(caprolactams), poly(acrylamides), poly(terephthalate), poly(vinyl chloride), poly(propylene), poly(ethylene oxide), poly(acrylic acid), poly(propylene oxide), poly(styrene), poly(ethylene), and poly(urethanes), and silicone elastomers. The aforementioned polymers can be in the form of homopolymers. Additionally, the aforementioned polymers can be in the form of polymer blends, alloys and copolymers. The polymer blends, alloys and copolymers can include combinations and mixtures of the aforementioned polymers. The copolymers can include random, block and graft copolymers. Poly(urethane) and poly(vinylpyrrolidone) are the most preferred polymers to be used with the present invention.

Natural polymers utilized in the present invention include, but are not limited to, cellulose, chitosan, chitin, starch, hyaluronic acid, chondroitin sulfate, zanthan, guar gum, and the like and the various ether and ester derivatives of these natural polymers. Additionally, the aforementioned polymers can be in the form of polymer blends or copolymers. The copolymers can include combinations and mixtures of the aforementioned polymers. The copolymers can include random, block and graft copolymers.

Preferred monomers of the present invention include, but are not limited to, acrylates, allylic compounds, amides, amines, anhydrides, epoxides, isocyanates, methacrylates, silyls, thiol compounds, vinyl compounds, esters, acid chlorides, acrolein, acryloylchlorides and thioisocyanates.

In one embodiment of the present invention, a polymer is preformed to which at least one radio-opaque moiety is covalently attached. In another embodiment a radio-opaque moiety is covalently attached to a monomer or copolymer from which a polymer is formed. The polymer can be formed from the polymerization of one type of monomer or copolymer; or the polymer can be formed from the polymerization of a blend of two or more different types of monomers or copolymers. In another embodiment, the monomer or copolymer with the attached radio-opaque moiety can be reacted with a preformed polymer.

For example, a monomer such as an diphenylmethane diisocyanate (MDI) can react by an amine linkage to the radio-opaque moiety as a first step, followed by derivatization of the second reactive site on the MDI with a polymer such as poly(vinyl pyrrolidone) (PVP) or by reaction with another isocyanate to form a polyurethane. In another example, a monomethacrylate or polymethacrylate can crosslink in the presence of ultraviolet radiation with a reactive site on the radio-opaque moiety, and additionally crosslink to a hydrophilic domain such a PVP, hydroxyethly cellulose (HEC), poly(vinyl alcohol) (PVA) or other acrylate monomers or polymers. Analogous bonding patterns are used for epoxides or other reactive groups.

The covalent attachment of the polymer or the monomer to the radio-opaque moiety can be through any type of covalent linkage. Examples of preferred covalent linkages include, but are not limited to, alkyl, amine, amide, anhydride, azide, carbamate, carboxyl, carbonate, ether, ester, imide, thiol, thiocarbamates, thioisocyanate, or urea linkage. The covalent attachment can be initiated by any type of chemical or non-chemical initiators. Examples of preferred initiators include the use of heat, ultraviolet irradiation, gamma irradiation, an acidic initiator, a basic initiator, a peroxide initiator, a persulfate initiator or an azo initiator. Additionally, a covalent linkage can be formed between the polymer or monomer and the radio-opaque moiety by graft-reacting.

The amount of a radio-opaque moiety attached to a polymer varies with the application of the radio-opaque composition. This amount can range from one molecule of the radio-opaque moiety attached to one monomer of the polymer, to a radio-opaque moiety attached to each monomer of the polymer.

The compositions of the present invention can further include at least one additional ingredient which is releasable or non-releasable from the compositions.

An additional ingredient can be incorporated into the composition by dissolving or suspending it in the composition. If the ingredient is suspended in the solution, it should be dispersed as fine particles ranging from 0.1–100 microns in average particle size.

An ingredient which is releasable is typically adsorbed or physically trapped in dry polymer. The ingredient is then released upon swelling. Additionally, a releasable ingredient can be ionically attached to PVP or other charged polymers.

An ingredient which is non-releasable from the composition typically has a component which is covalently attached to the composition. Alternately, this non-releasable ingredient is embedded in a polymeric matrix which impedes the release of the ingredient.

These additional ingredients can be biologically active materials. A biologically active material is any bio-effecting agent or bio-treating agent.

Generally, biologically active materials used according to this invention can include, but are not limited to, for example: antibacterial and antimicrobial agents; anticoagulant and antithrombotic agents; platelet agents; anti-inflammatories; enzymes; catalysts; hormnones; growth factors; drugs; vitamins; antibodies; antigens; nucleic acids; dyes (which act as biological ligands); DNA and RNA segments; biostatic agents; cytostatic agents; radiation emitters; biomolecules; immunosuppressants; antiseptics; and proteins and peptides. Further examples include heparin, prostaglandin $E_1$, ticlopidine, plasmin, urokinase, oligonucleotides, TPA, polyethylene oxide (PEO), and FUT-175. Preferred biologically active materials are antibiotics and antithrombotic agents. The biologically active materials can be synthetically derived or naturally occurring. The biologically active material can include molecules of one of the aforementioned materials or it can include molecules of two or more of the materials.

The concentration or loading of the biologically active material can be varied according to the therapeutic effects desired. Also, the loading, in terms of the ratio of biologically active material to polymer or monomer, will depend upon the efficacy of the polymer or monomer in securing the biologically active material onto itself and the rate at which the coating is to release the biologically active material to the body tissue. Generally, the polymer can contain 0.01–90% by weight, preferably 1.0–45% by weight, and most preferably, 2.5–25% by weight of the biologically active material.

The present invention includes compositions which have a low coefficient of friction when wetted with water or a water-containing substance. Polymer and monomer blends which exhibit useful degrees of hydrophilicity also exhibit significantly reduced coefficients of friction when wet. Such blends contain, for example, a sufficient quantity of poly(N-vinyl lactam) or HEC. For example, the compositions of the present invention can further include a polyvinylpyrrolidone-polyurethane complex. This complex can be reacted or alloyed into the composition. It is known in the prior art to complex a polyurethane with polyvinylpyrrolidone. The exact nature of the complex is not known, but the polyvinylpyrrolidone is, in any event, bound to the polyurethane in a form which is referred to in the art as a complex (some refer to this particular complex as an interpolymer). These complexes and the manner of making them are well-known to the art as seen, for example, in U.S. Pat. Nos. 4,100,309; 4,769,013; 6,054,504 and 4,642,267. These patents are incorporated herein by reference. The polyvinylpyrrolidone-polyurethane complex can further include a biologically active material.

Typical polyvinylpyrrolidone-polyurethane complexes are polyvinylpyrrolidone complexed with polytetramethylene ether glycol-diphenylmethane diisocyanate (MDI), polytetramethylene ether glycol-tolylene diisocyanate (TDI), polytetramethylene ether glycol-isophorone diisocyanate, poly(1,4-oxybutylene) glycol-diphenylmethane diisocyanate (MDI), poly(1,4-oxybutylene) glycol-tolylene diisocyanate (TDI), poly(1,4-oxybutylene) glycol-isophorone diisocyanate, polyethylene glycol-diphenylmethane diisocyanate (MDI), polyethylene glycol-tolylene diisocyanate (TDI), polyethylene glycol-isophorone diisocyanate, polypropylene glycol-diphenylmethane diisocyanate (MDI), polypropylene glycol-tolylene dilsocyanate (TDI), polypropylene glycol-isophorone diisocyanate, polycaprolactone-diphenylmethane diisocyanate (MDI), polycaprolactone-tolylene diisocyanate (TDI), polycaprolactone-isophorone diisocyanate, polyethylene adipate-diphenylmethane diisocyanate (MDI), polyethylene adipate-tolylene diisocyanate (TDI), polyethylene adipate-isophorone diisocyanate, polytetra-methylene adipate-diphenylmethane diisocyanate (MDI), polytetramethylene adipate-tolylene diisocyanate (TDI), polytetramethylene adipate-isophorone diisocyanate, polyethylene-propylene adipate-diphenylmethane diisocyanate (MDI), polyethylene-propylene adipate-tolylene diisocyanate (TDI), or polyethylene-propylene adipate-isophorone diisocyanate polyurethanes.

The present invention includes any of the compositions and methods of coating as discussed in, for example, Fan, et al., [*Polymer News*, 1992, 17, 70–74], Ikada, Y., and Uyama, Y., in "Lubricating Polymer Surfaces", Technomic, Lancaster, Pa., 1993, and LaPorte, R., "Hydrophilic Polymer Coatings For Medical Devices", Technomic, Lancaster, Pa., 1997, these references being incorporated in their entirety into the present invention.

In one embodiment the compositions further include a solvent. Suitable solvents are ones which can dissolve the composition into solution but do not alter or adversely impact the therapeutic properties of the biologically active material employed in the composition. Additionally, the solvents themselves should preferably be free of reactive amino, hydroxyl and carboxyl groups. Preferred solvents include, for example, dichloromethane, methyl ethyl ketone, acetone, ethyl lactate, chloroform, tetrahydrafuran (THF), trichloroethylene, mono and diethylene glycol ethers, N-methyl pyrrolidone, diacetone alcohol, methyl chloride and ethyl acetate. The hydroxyl of the ethyl lactate is not sufficiently reactive to be detrimental. Although the solvents preferably do not contain reactive groups, solvents such as water, aqueous alcohol mixtures and alcohols are suitable for the practice of the present invention for certain monomers and polymers.

The compositions of the present invention can be used to provide radio-opaque objects. Objects for the purposes of this invention include, but are not limited to, devices and materials used in the medical or industrial fields. In one embodiment the material of which the radio-opaque object is composed includes the composition of the present invention. In another embodiment the compositions of the present invention can be used as covering compositions for objects. These covering compositions include coatings and primers. The present invention also provides a method by which to render objects radio-opaque and radio-opaque objects.

In a preferred embodiment of the coatings a radio-opaque moiety is covalently attached to a polymer, such as those aforementioned. The coatings of the present invention can include a single type of polymer. Alternately, the coatings can include a blend of polymers. The appropriate blend of polymers can be coordinated with the particular application of the coating. For example, in the medical field the blend can be coordinated with the particular biologically active material to produce the desired effects. The amount of the radio-opaque moiety included in a coating is the amount necessary to render the object, to which the coating is applied, sufficiently radio-opaque. Such an amount can vary based on the material of the object, evaluation technique and environment.

In a preferred embodiment of the primers a radio-opaque moiety is covalently attached to a monomer, such as those aforementioned. The primers of the present invention can include a single type of monomer. Alternately, the primers can include a blend of monomers. The appropriate blend of monomers can be coordinated with the particular application of the primer. For example, in the medical field the blend can be coordinated with the particular biologically active material to produce the desired effects. Each monomer can have a radio-opaque moiety covalently attached. Alternately, the radio-opaque moiety can be covalently attached to only some of the monomers making up the primer in the amount necessary to render the substrate, to which the primer is applied, radio-opaque.

In one embodiment the monomers of the primer can directly react or bind to a surface of the object to which the primer is applied. A reaction or binding to the surface of an object can occur when the object is made of a material which has reactive functional groups. For example, in the case of an object made of polyurethane, the primer can covalently cross link to the object. In another embodiment the monomer adheres to a surface of the object to which the primer is applied. Adhesion is a physical bond by, for example, entrapment, entanglement, hydrogen bonding, van der Waals forces or other forces. For example, in the case of an object made of steel, the monomers making up the primers would form a polyurethane and adhere to steel.

The present invention includes an embodiment wherein after the application of the primer to an object, a coating can be further applied. The primer allows for a durably and tenaciously adhered coating on plastic, ceramic or metal objects.

The covering compositions can include the aforementioned additional ingredients. Preferred additional ingredients used with medical devices are antithrombotic agents and antibiotics. The covering compositions can also include ingredients to lower the coefficient of friction of the composition as stated above.

In one embodiment the covering compositions include a solvent, such as those aforementioned. The method of the invention includes applying the covering composition in a solvent to the surface of the object to be coated and then removing the solvent. The solvent is removed preferably by evaporation.

The covalent linkage between the monomer or polymer and the radio-opaque moiety can be formed as a solvent is removed. Alternately, the covalent linkage can be formed during formulation of the covering composition.

One embodiment of the invention is an object modified with a covering which includes a polymer or monomer having a non-leachable radio-opaque moiety. The objects that can be modified by the method of the present invention can be made of many different materials. These materials include, but are not limited to: metals such as titanium/titanium alloys, TiNi (shape memory/super elastic), aluminum oxide, platinum/platinum alloys, stainless steels, MP35N, elgiloy, haynes 25, stellite, pyrolytic carbon, silver, glassy carbon, tantalum, nickel-chrome, cobalt-chromium; polymers such as polyurethanes, polycarbonates, silicone elastomers, polyolefins including polyethylenes or polypropylenes, polyvinyl chlorides, polyethers, polyesters, nylons, polyvinyl pyrrolidones, polyacrylates and polymethacrylates such as polymethylmethacrylate (PMMA), n-Butyl cyanoacrylate, polyvinyl alcohols, polyisoprenes, rubber, cellulosics, polyvinylidene fluoride (PVDF), polytetrafluoroethylene, poly(p-phenyleneterephthalamide, ethylene tetrafluoroethylene copolymer (ETFE), acrylonitrile butadiene ethylene, polyamide, polyimide, styrene acrylonitrile, and the like; minerals or ceramics such as hydroxapatite; human or animal protein or tissue such as bone, skin, teeth, collagen, laminin, elastin or fibrin; organic materials such as wood, cellulose, or compressed carbon; and other materials such as glass, or the like. Additionally, objects can be made of biologically active components, such as, for example, triclosan, cetylpyridinium chloride, hexidene, chlorohexidene or the like.

The object of the present invention includes any device or material used in the industrial or medical fields.

Examples of devices used in the industrial fields upon which the covering composition of the present invention can be used include, but are not limited to, computer CRT and probes for in-process reactions. For example, nanochips can be tracked in nuclear and bioreactors by coverings the nanochips with the covering composition of the present invention. In addition, the radio-opaque devices of the present invention can be used as, for example, traceable catalytic devices in bioreactors where the removal of the catalyst from the reaction broth can be traced by monitoring the radio-opaque catalyst; traceable electronic devices used, for example, in animal monitoring; x-ray opaque tracking systems for explosives and other hazardous materials, especially as airport security scanners; and other industrial applications that require the use of high energy electromagnetic radiation sensitive monitoring devices, especially where filmed images are used.

A medical device is any object having surfaces that contact tissue, blood or other bodily fluids in the course of its operation, which fluids are subsequently used in a living body. Medical devices in which the biocompatible composition of the present invention can be incorporated include, but are not limited to, surgical implants, prostheses, and any artificial part or device which replaces or augments a part of a living body or comes into contact with bodily fluids, particularly blood. The objects can be in any shape or form including tubular, sheet, rod and articles of proper shape. Various medical devices and equipment usable in accordance with the invention are known in the art. Examples of devices include catheters, suture material, tubing, and fiber membranes. Examples of catheters include central venous catheters, thoracic drain catheters, angioplasty balloon catheters. Examples of tubing include tubing used in extracorporeal circuitry, such as whole blood oxygenators. Examples of membranes include polycarbonate membranes, haemodialysis membranes, membranes used in diagnostic or biosensor devices. Also included are devices used in diagnosis, as well as polyester yarn suture material such as polyethylene ribbon, and polypropylene hollow fiber membranes.

Further illustrations of medical devices include the following: autotransfusion devices, blood filters, blood gas exchange devices, blood pumps, blood temperature monitors, bone growth stimulators, breathing circuit connectors, bulldog clamps, cannulae, grafts, implantible pumps, impotence and incontinence implants, intraoccular lenses, leads, lead adapters, lead connectors, nasal buttons, orbital implants, cardiac insulation pads, cardiac jackets, clips, covers, dialators, dialyzers, disposable temperature probes, domes, drainage products, drapes, ear wicks, electrodes, embolic devices, esophageal stethoscopes, fracture fixation devices, gloves, guide wires, hemofiltration devices, hubs, intra-arterial blood gas sensors, intracardiac suction devices, intrauterine pressure devices, nasal spetal splints, nasal tampons, needles, ophthalmic devices, oxygenators (both sheet and tubular forms of membrane oxygenators), PAP brushes, periodontal fiber adhesives, pessary, pins, retention cuffs, screws, sheeting, sponges, staples, stomach ports, surgical instruments, transducer protectors, ureteral stents, vaginal contraceptives, valves, vessel loops, water and saline bubbles, achtabular cups, annuloplasty ring, aortic/coronary locators, artificial pancreas, balloons, batteries, bone cement, breast implants, cardiac materials, such as fabrics, felts, films, markers, mesh, patches, cement spacers, cochlear implant, defibrillators, generators, orthopedic implants, pacemakers, patellar buttons, penile implant, pledgets, plugs, plates, ports, prosthetic heart valves, sheeting, shunts, stylets, umbilical tape, valved conduits, and vascular access devices.

The method of the present invention is particularly applicable to stents. A stent, for the purposes of this specification, is any device capable of being delivered by catheter. Stents include balloon-expandable and self-expanding stents. The balloon-expandable stent includes the metallic coils and slotted tube designs.

A preferred stent to be used with the present invention is described in Canadian Patent No. CA 2201001 ((Plante) which is incorporated herein by reference. This stent is a longitudinally flexible permanent intravascular prosthesis, made of a plastically deformable metal alloy, for implantation in a body lumen and expandable from a contracted condition to an expanded condition. The stent contains a plurality of adjacent rings independently expandable in the radial direction and interconnecting members between adjacent rings. The stent includes two types of rings, each formed by a plurality of either hexagonal or inverted hexagonal elements. The two types of rings are arranged alternately in alignment over the longitudinal axis of the stent. Two interconnecting members are used to join adjacent rings, positioned at 0° and 180° in the traverse axis to provide flexibility between two rings in one plane; the next pair of interconnecting members is shifted 90° from the previous one to provide flexibility to the next attached ring in the perpendicular plane. The stent is mounted and crimped over a balloon catheter, delivered in a contracted state within a body lumen such as an artery and expanded passively by the radial forces on the inflating balloon catheter.

Other suitable stents include a deformable metal wire stent useful as a stent framework, such as that described in U.S. Pat. No. 4,886,062 (Wiktor), which discloses preferred methods for making a wire stent. Other useful metallic stents include those of U.S. Pat. Nos. 4,733,655 (Palmaz) and 4,800,882 (Gianturco). Other suitable stents include the Palmaz-Schatz coronary stent (Johnson & Johnson Interventional, Warren, N.J.) and stents from memory-shaped metals such as selfexpanding nitinol stents including that available under the trade designation CARDIOCOIL from Medtronic, Eden Prairie, Minn., and disclosed in U.S. Pat. No. 5,372,600. Preferred stents for use in this invention should be flexible to navigate lumens during insertion, biocompatible, and reliably expand and embed in the lumen wall.

The stent is treated with the covering composition according to the present invention. The stent includes a lumen wall-contacting surface and lumen-exposed surface. Where the stent is shaped generally as a tube-like structure, including a discontinuous tube or ring-like structure, the lumen-wall contacting surface is the outside surface of the tube and the lumen-exposed surface is the inner surface of the tube. When in place, the outer surface is in contact with a portion of a wall of a lumen, and the inner surface is in contact with blood. Typically, both the lumen wallcontacting surface and the lumen-exposed surface are coated with the covering composition, although, depending on the materials used to make the stent, only the lumen-exposed surface would need to be.

The present invention provides a method of rendering an object radio-opaque. The method includes applying a covering composition of the present invention to an object. The covering composition can be applied to an object with or without a solvent. If the covering composition is applied in a solvent, it is evaporated. The covering composition can be applied by spraying, dipping, plasma vapor deposition, flow coating, brushing or dabbing.

Additionally, a covering composition can be applied by melt extruding. In this embodiment the composition is thermoplastic or thermosetting and no solvent is used.

For example, a wiring can be drawn through such a covering composition in a manner so that a covering is formed on the wire.

The covering composition is applied to an object to a thickness that will render an object sufficiently radio-opaque for the particular application. Coating thickness can be from about 0.1 microns or thicker.

In plasma vapor deposition the coating composition is applied to an object in an atmosphere of some inert gas such as argon. While the technique can use nonelectrical apparatus, it is preferred that the plasma be created electrically. The method is commonly known as sputtering. Plasma for the purposes of this specification means an ionized gas created in a d.c. or radio-frequency a.c. field for the purpose of sputtering atoms from a target onto a substrate. Vapor as used herein means a cloud of atomic particles created in a low pressure atmosphere by means of thermal evaporation or an electron gun, the vapor condensing on the surface of the substrate. Accordingly, "plasma vapor" means the cloud of particles created by sputtering or evaporation.

In spraying the covering compositions onto an object, different coating thicknesses can be readily achieved by adjusting the number of spray cycles. Typically, an airbrush such as a Badger Model 150 (supplied with a source of pressurized air) can be used. If a significant amount of surface area is to be coated, it may be preferable to place the object in a rotating fixture to facilitate the coverage of the object's surface. For example, to coat the entire surface of a vascular stent, the ends of the device are fastened to a rotating fixture by resilient retainers, such as alligator clips. The stent is rotated in a substantially horizontal plane around its axis. The spray nozzle of the airbrush is typically placed 2–4 inches from the device.

The thickness of the covering composition can be adjusted by the speed of rotation and the flow rate of the spray nozzle. The speed of rotation is usually adjusted at about 30–50 rpm, typically at about 40 rpm. The flow rate of the spray nozzle, which can range from 4–10 ml coating per minute may also be adjusted. Usually, a number of spraycoats will be required to achieve the desired covering thickness. If a non-spray process is utilized, such as dipping then one coat may be sufficient.

EXAMPLES

The following Examples are intended to show the practice of the invention and are not intended to restrict the scope of the present invention. All percentages are in weight/volume unless otherwise indicated.

Example 1

Incorporation of the Radio-opaque Moiety into a Coating Through a Reactive Polymer.

A poly(urethane) stent was cleaned with isopropyl alcohol and dried in an oven at 60° C. A dipping solution was prepared by first predispersing iodopanoic acid in dimethylacetamide to afford a 10% solution. The predispersion was then added at a 20% level to a methyl ethyl ketone solution containing 2% of equal weights of a 32% solution of poly(caprolactone)/toluene diisocyanaate polyurethane in ethyl acetate (available from Lord Chemical as Flock-Lok 7000) and a 40% solution of the adduct trimethylolpropane-diphenyl methane diisocyanate in methyl ethyl ketone (available commercially from Lord as Flock-Lok 7200).

The stent was dipped into the solution above for one hour, air dried for several minutes and then redipped as described. The process was repeated several times to assure a consistent coating. The treated stent was then dipped into a 4% solution of poly(vinylpyrollidone), (Mw approx. 1.200,000) previously dissolved in ethyl acetate. The thus coated stent was removed, air dried for several minutes and oven cured at 65° C. for 6 hrs. The resulting stent showed improved visualization properties compared to an uncoated stent when viewed, via a fluoroscope through a porcine test subject.

Example 2

Reaction of the Radio-opaque Moiety Through Reactive Isocyanate Monomer.

A 14 Fr., intermittent urinary catheter was thoroughly cleaned using isopropyl alcohol and oven dried at 60° C. for five minutes. A 10% predispersion was made using iodopanoic acid and dimethylacetamide. A second mixture was made by combining the ingredients shown in Table 1.

TABLE 1

| Ingredient | Amount | Source |
|---|---|---|
| Trepol | 1.0 gram | Rynel Corp |
| Dimethylacetaamide | 7.0 gram | Fisher |
| Iodopanoic acid dispersion | 2.0 grams | see above |
| Kollidon K-90 | 3.0 grams | BASF |
| Ethyl acetate | 15 grams | Fisher |
| Methyl Ethyl Ketone | 25 grams | Aldrich |

The catheter was dipped into the above coating mixture for 9 seconds, air dried for 15 min., and subsequently oven dried for 30 minutes at 80° C. The resulting tubing was examined via a fluoroscope and showed superior radio-opacity compared to a catheter similarly coated which did not have the radio-opaque moiety included.

Example 3

Reaction of Radio-opaque Moiety with a Reactive Monomer and Coating on a Catheter.

A 12 Fr., latex catheter was cleaned as described in Example 2. A 20% predispersion of iodopanoic acid in dimethylacetamide was prepared as described above. To the predispersion was added 4,4-Diphenylmethyl diisocyanate (Mondur M, Bayer Corp) such that the ratio of the reactive isocyanate to radio-opaque moiety was greater than 1:1 using the formulation shown in Table 2:

| Ingredient | Amount |
|---|---|
| Mondur M | 4.0 gram |
| Methylene Chloride | 28 gram |
| Iodopanoic acid predispersion | 28 gram |

The resulting radio-opaque coated catheter showed superior visualization compared to a similarly prepared catheter that was not reacted with the reactive radio-opaque monomer.

Example 4

Preparation of a Radio-opaque Lubricious Catheter Coating.

The reactive monomer composition above was coated as described onto a similar catheter as described in Example 3. The coated, dry catheter was then dipped into a 2.5% solution of poly(vinylpyrollidone), (Kollidon K-90, BASF) in ethyl acetate. The catheter was dipped into this mixture for 15 minutes, removed and air dried for 3 minutes. The catheter was dried in a force draft oven at 60° C. for 30 minutes. The resulting radio-opaque coated catheter showed superior visualization compared to a similarly prepared catheter that was not reacted with the reactive radio-opaque monomer of Example 3. In addition, the catheter showed superior wet lubricity compared to the catheter of Example 3.

Example 5

Preparation of Radio-opaque Coating Using Reactive Monomer and a Cellulose Derivative.

A 14 Fr., polyurethane dialysis catheter was cleaned as described in Example 3. A formulation was prepared by combining the ingredients shown in Table 3. The reactive radio-opaque monomer predispersion was prepared at 15% active solids as described in Example 3.

TABLE 3

| Ingredient | Amount | Source |
| --- | --- | --- |
| Poly(vinylpyrollidone), 1,200,000 Mw | 0.006 gram | BASF |
| 2-Propanol | 1.0 gram | Fisher |
| Nitrocellulose | 1.5 gram | ICI |
| Ethyl acetate | 1.0 gram | Fisher |
| Hydrogenated rosin ester | 0.5 gram | Hercules |
| Iodopanoic acid monomer | 0.5 gram | Example 3 |
| Ethyl-3-ethoxy propionate | 6.1 gram | Charles Tennant & Co. |

The catheter was dipped into the mixture above for 15 minutes, removed and air dried for 3 minutes and then oven dried in a force draft oven at 60° C. for 30 minutes. The resulting catheter showed superior x-ray visualization properties compared to a similarly prepared catheter that did not contain the radio-opaque monomer.

Example 6

Reaction of Radio-opaque Monomer with a UV-curable Lubricious Coating

A 14 Fr., poly(urethane) catheter was washed as described in Example 2. A 20% dispersion of iodopanoic acid and 4,4-diphenylmethyl diisocyanate in dimethylacetamide was prepared as described in Example 3. A mixture of 10.0 g of N-vinylpyrrolidone, 10 g trimethylolpropane monoacrylate, 4.0 g PVP and 0.75 g of UV-sensitive photoinitiator (Darocur 1116, Merck) was prepared. To this mixture was added 2.0 grams of the reactive radio-opaque predispersion. The catheter was dipped into the reactive mixture and the coated catheter was irradiated with UV light using an 80 W UV lamp for 45 seconds. Simultaneously, the catheter was irradiated with an infrared lamp such that the temperature of exposure was 60° C. The catheter was exposed to the IR radiation for an additional 30 minutes. The resulting coated catheter was found to possess superior radio-opacity compared to a similarly coated catheter without the radio-opaque monomer.

Example 7

Reaction of a Radio-opaque Monomer with a Plasma Prepared Catheter Using a Poly(Ethylene Oxide)/Polyacrylate Coating.

A 14 Fr., PEBAX catheter (Atochem) was cleaned with VM& P naptha and oven dried at 60° C. for 5 minutes. The resulting catheter was placed into a plasma chamber that contained an ammonia atmosphere at $10^{31}$ $^3$ Torr and the surface was plasma etched for 15 minutes. A 10% predispersion of the radio-opaque monomer in dimethylacetamide was prepared as described in Example 3. An 2.5% aqueous coating solution was prepared using a blend of a polyacrylate (BF Goodrich) and a 600 Mw poly(ethylene oxide), (Union Carbide), such that the ratio of acrylate to PEO was 2:1. To this coating composition was added 25% of the radio-opaque monomer predispersion and the entire mixture was blended with 1 stoichiometric equalivent of aziridine (ethyleneimine). The catheter was dipped into the coating solution for 10 seconds, dried for 15 minutes and subsequently oven dried in a force draft oven at 80° C. for 30 minutes. The resulting catheter showed superior performance compared to a similarly prepared catheter that did not contain the radio-opaque monomer.

Example 8

Reaction of Radio-opaque Monomer with a Glycidylmethacrylate Coating.

An 8 Fr., polyurethane catheter tube was cleaned as described in Example 2. A 20% predispersion of the radio-opaque monomer was prepared as described in Example 3. A block copolymer of dimethylacrylamide and glycidyl methacrylate was prepared by reacting these two monomers together using a polyperoxide initiator. The polymerization was conducted at 80° C. for 2 hours. A 2% solution of the resulting copolymer was prepared in methyl ethyl ketone and 25% of the radio-opaque monomer dispersion was added to the polymer mixture. The catheter tube was placed into the coating formulation above for 10 seconds, air dried for 15 minutes and oven dried at 80° C. for 30 minutes. The resulting tube showed superior x-ray visualization properties compared to a tube prepared from a similar formulation that did not contain the radio-opaque monomer.

What is claimed is:

1. A radio-opaque composition comprising a polymer or monomer, and an antithrombotic, wherein said polymer or monomer has a non-leachable radio-opaque moiety, wherein said non-leachable radio-opaque moiety is covalently attached to said polymer or said monomer, and wherein said antithrombotic agent is releasable or non-releasable from said composition.

2. A radio-opaque primer comprising a monomer, wherein said monomer has a non-leachable radio-opaque moiety, wherein said monomer has at least one reactive functional group, wherein said reactive functional group is an isocyanate, an isothiocyanate, an ester, an aldehyde, an N-hydroxysuccinimide ester, an epoxide, a carboxylic ester, a tresylate, an anhydride, an alkyl halide, a carboxylic acid, a haloketone, an alkene, an alkyne or an acyl chloride; and wherein said monomer is covalently attached to an object by a covalent linkage.

3. The radio-opaque composition of claim 1, wherein said polymer is a natural polymer or a synthetic polymer or a combination thereof; wherein said synthetic polymer is a polymer blend, alloy, random copolymer, block copolymer, graft copolymer or homopolymer; and wherein said synthetic polymer comprises poly(vinyl alcohol), poly (vinylpyrrolidone), poly(caprolactone), poly (hydroxybutarates), poly(caprolactams), poly (terephthalate), poly(vinyl chloride), poly(propylene), poly (ethylene oxide), poly(propylene oxide), poly(styrene), poly (ethylene), poly(urethanes), silicone elastomers or combinations thereof; wherein said monomer is an allyllic compound, amide, amine, anhydride, epoxide, isocyanate, silyl, thiol compound, thioisocyanate, vinyl compound, ester, acid chloride, acrolein or acryloylchloride; wherein said polymer or said monomer has at least one reactive functional group, wherein said reactive functional group is an isocyanate, an isothiocyanate, an epoxide, a carboxylic ester, a tresylate, an anhydride or a carboxylic acid; and wherein said non-leachable radio-opaque moiety is covalently attached to said polymer or said monomer.

4. A radio-opaque primer of claim 2, wherein said monomer is an allyllic compound, amide, amine, anhydride, epoxide, isocyanate, silyl, thiol compound, thioisocyanate, vinyl compound, ester, acid chloride, acrolein or acryloylchoride.

5. A radio-opaque composition comprising:
(a) a polymer or monomer, wherein said polymer or monomer has a non-leachable radio-opaque moiety, and
(b) a polyvinylpyrrolidone-polyurethane complex, wherein said polymer is a natural polymer or a synthetic polymer or a combination thereof; wherein said synthetic polymer is a polymer blend, alloy, random copolymer, block copolymer, graft copolymer or homopolymer; wherein said synthetic polymer comprises poly(vinyl alcohol), poly(vinylpyrrolidone), poly(caprolactone), poly(hydroxybutarates), poly (caprolactams), poly(terephthalate), poly(vinyl chloride), poly(propylene), poly(ethylene oxide), poly (propylene oxide), poly(styrene), poly(ethylene), poly (urethanes), silicone elastomers or combinations thereof; wherein said monomer is an allyllic compound, amide, amine, anhydride, epoxide, isocyanate, silyl, thiol compound, thioisocyanate, vinyl compound, ester, acid chloride, acrolein or acryloylchoride; and wherein said polymer or said monomer has at least one reactive functional group, wherein said reactive functional group is an isocyanate, an isothiocyanate, an epoxide, a carboxylic ester, a tresylate, an anhydride or a carboxylic acid; and wherein said non-leachable radio-opaque moiety is covalently attached to said polymer or said monomer.

6. A composition according to claim 5 wherein said radio-opaque moiety is a halogenated aromatic compound with a reactive functional group.

7. A composition according to claim 6 wherein said halogenated aromatic compound is an aromatic tri-iodide or an aromatic tri-bromide.

8. A composition according to claim 6 wherein said reactive functional group of said radio-opaque moiety is a hydroxyl, a carboxyl, an amine, an amide, a carbonyl, a thiol, an allyl, a vinyl or an anhydride.

9. A composition according to claim 2 wherein said radio-opaque moiety is an amidotrizoate, an iothalamate, an iohexol, an iopamidol, an iopromide, ioxaglic acid, an iopadate, an iotroxate or an ioxaglate.

10. A composition according to claim 5 wherein said radio-opaque moiety is Iobenguane, Iobenzamic Acid, Iocarmic Acid, Iocetamic Acid, Iodamide, Iodipamide, Iodixanol, Iodized Oil, Iodoalphionic Acid, p-Iodoaniline, o-Iodobenzoic Acid, Iodochlorhydroxyquin, o-Iodohippurate Sodium, o-Iodophenol, p-Iodophenol, Iodophthalein Sodium, Iodopsin, Iodopyracet, Iodopyrrole, Iodoquinol, Iofetamine $^{123}$I, Ioglycamic Acid, Iohexol, Iomeglamic Acid, Iopamidol, Iopanoic acid, Iopentol, Iophendylate, Iophenoxic Acid, Iopromide, Iopronic Acid, Iopydol, Iopydone, Iothalamic Acid, Iotrolan, Ioversol, Ioxaglic Acid, Ioxilan, or Ipodate.

11. A composition according to claim 5 wherein said natural polymer is a cellulose, chitosan, chitin, starch, hyaluronic acid, chondroitin sulfate, xanthan, guar gum; or an ether or an ester derivative thereof; or a block, a graft or random copolymer thereof; or a blend thereof.

12. A composition according to claim 5 wherein said radio-opaque moiety is covalently attached to said polymer or said monomer through an amine, amide, anhydride, carbamate, carbonate, carboxyl, ether, ester, imide, thiol, thiocarbamates, or urea covalent linkage.

13. A composition according to claim 5 wherein said radio-opaque moiety is covalently attached to said polymer or said monomer by the use of heat, ultraviolet irradiation, gamma irradiation, an acidic initiator, a basic initiator, a peroxide initiator, a persulfate initiator or an azo initiator.

14. A composition according to claim 5 further comprising at least one additional ingredient wherein said additional ingredient is releasable or non-releasable from said composition.

15. A composition according to claim 14 wherein said additional ingredient is a biologically active material.

16. A composition according to claim 15 wherein said biologically active material is a biostatic agent, a cytostatic agent, a radiation emitter, a biomolecule, an anti-inflammatory agent, an immunosuppressant or an antiseptic.

17. A composition according to claim 15 wherein said biologically active material is an antibiotic.

18. A composition according to claim 15 wherein said biologically active material is an antithrombotic agent.

19. A composition according to claim 5 wherein said composition has a low coefficient of friction when wetted with water or a water-containing substance.

20. A composition according to claim 5 further comprising a solvent.

21. A composition according to claim 20 wherein said covalent linkage is formed as said solvent is removed.

22. A composition according to claim 5 wherein said covalent linkage is formed during formulation of said composition.

23. A composition according to claim 5 wherein said composition is a covering composition.

24. A covering composition according to claim 23 wherein said covering composition is a coating.

25. A covering composition according to claim 23 wherein said covering composition is a primer.

26. A composition according to claim 25 wherein said primer is a blend of said monomers.

27. A primer according to claim 25 wherein said monomer is covalently attached to an object by a covalent linkage.

28. A primer according to claim 25 wherein said monomer adheres to an object.

29. A radio-opaque primer comprising a monomer which is covalently attached to a non-leachable radio-opaque moiety, wherein said monomer is an allyllic compound, amide, amine, anhydride, epoxide, isocyanate, silyl, thiol compound, thioisocyanate, vinyl compound, ester, acid chloride, acrolein or acryloylchoride; and wherein said monomer has at least one reactive functional group selected from the group consisting of an isocyanate, an isothiocyanate, an epoxide, a carboxylic ester, a tresylate, an anhydride and a carboxylic acid; wherein said monomer adheres to an object.

30. A medical device covered with a composition comprising:
(a) a polymer or a monomer wherein said polymer or said monomer has a non-leachable radio-opaque moiety, and
(b) a polyvinylpyrrolidone-polyurethane complex, wherein said radio-opaque moiety is a halogenated aromatic compound with a reactive functional group; wherein said polymer is a natural polymer or a synthetic polymer or a combination thereof, wherein said synthetic polymer is a polymer blend, alloy, random copolymer, block copolymer, graft copolymer or homopolymer; wherein said synthetic polymer comprises poly(vinyl alcohol), poly(vinylpyrrolidone), poly(caprolactone), poly(hydroxybutarates), poly(caprolactams), poly(terephthalate), poly(vinyl chloride), poly(propylene), poly(ethylene oxide), poly(propylene oxide), poly(styrene), poly(ethylene), poly(urethanes), silicone elastomers or combinations thereof; wherein said monomer is an allyllic compound, amide, amine, anhydride, epoxide, isocyanate, silyl, thiol compound, thioisocyanate, vinyl compound, ester, acid chloride, acrolein or acryloylchoride; and wherein said polymer or said monomer has at least one reactive functional group, wherein said reactive functional group is an isocyanate, an isothiocyanate, an epoxide, a carboxylic ester, a tresylate, an anhydride, or a carboxylic acid.

31. A medical device according to claim 30 wherein said medical device is a catheter, guide wire, shunt, screw, pin, prosthesis, plate, film, sponge, suture, tube, cannula, balloon, needle, marker or stylet.

32. A stent covered with a composition comprising:
(a) a polymer or a monomer wherein said polymer or said monomer has a non-leachable radio-opaque moiety, and
(b) a polyvinylpyrrolidone-polyurethane complex, wherein said radio-opaque moiety is a halogenated aromatic compound with a reactive functional group; wherein said polymer is a natural polymer or a synthetic polymer or a combination thereof; wherein said synthetic polymer is a polymer blend, alloy, random copolymer, block copolymer, graft copolymer or homopolymer; wherein said synthetic polymer comprises poly(vinyl alcohol), poly(vinylpyrrolidone), poly(caprolactone), poly(hydroxybutarates), poly(caprolactams), poly(terephthalate), poly(vinyl chloride), poly(propylene), poly(ethylene oxide), poly(propylene oxide), poly(styrene), poly(ethylene), poly(urethanes), silicone elastomers or combinations thereof; wherein said monomer is an allyllic compound, amide, amine, anhydride, epoxide, isocyanate, silyl, thiol compound, thioisocyanate, vinyl compound, ester, acid chloride, acrolein or acryloylchoride; and wherein said polymer or said monomer has at least one reactive functional group, wherein said reactive functional group is an isocyanate, an isothiocyanate, an epoxide, a carboxylic ester, a tresylate, an anhydride, or a carboxylic acid.

33. A method of rendering an object radio-opaque comprising: applying a composition to said object, wherein said composition comprises:
(a) a polymer or monomer wherein said polymer or said monomer has a non-leachable radio-opaque moiety and
(b) a polyvinylpyrrolidone-polyurethane complex, wherein said polymer is a natural polymer or a synthetic polymer or a combination thereof, wherein said synthetic polymer is a polymer blend, alloy, random copolymer, block copolymer, graft copolymer or homopolymer, wherein said synthetic polymer comprises poly(vinyl alcohol), poly(vinylpyrrolidone), poly(caprolactone), poly(acrylamides), poly(hydroxybutarates), poly(caprolactams), poly(terephthalate), poly(vinyl chloride), poly(propylene), poly(ethylene oxide), poly(acrylic acid), poly(propylene oxide), poly(styrene), poly(ethylene), poly(urethanes), silicone elastomers or combinations thereof; wherein said monomer is an acrylate, allyllic compound, amide, amine, anhydride, epoxide, isocyanate, methacrylate, silyl, thiol compound, thioisocyanate, vinyl compound, ester, acid chloride, acrolein or acryloylchoride; and wherein said polymer or said monomer has at least one reactive functional group, wherein said reactive functional group is an isocyanate, an isothiocyanate, an epoxide, a carboxylic ester, a tresylate, an anhydride or a carboxylic acid.

34. A method of rendering an object radio-opaque comprising: applying a radio-opaque primer to said object, wherein said primer comprises a monomer, wherein said monomer has a non-leachable radio-opaque moiety, wherein said monomer has at least one reactive functional group, wherein said reactive functional group is an isocyanate, an isothiocyanate, an ester, an aldehyde, an N-hydroxysuccinimide ester, an epoxide, a carboxylic ester, a tresylate, an anhydride, an alkyl halide, a carboxylic acid, a haloketone, an alkene, an alkyne or an acyl chloride; and wherein said monomer is covalently attached to an object by a covalent linkage.

35. A method of rendering an object radio-opaque comprising: applying a primer to said object, wherein said primer comprises a monomer which is covalently attached to a non-leachable radio-opaque moiety, and a a polyvinylpyrrolidone-polyurethane complex; wherein said monomer is an allyllic compound, amide, amine, anhydride, epoxide, isocyanate, silyl, thiol compound, thioisocyanate, vinyl compound, ester, acid chloride, acrolein or acryloylchoride; and wherein said monomer has at least one reactive functional group selected from the group consisting of an isocyanate, an isothiocyanate, an epoxide, a carboxylic ester, a tresylate, an anhydride and a carboxylic acid; wherein said monomer adheres to an object.

36. An object covered with a composition comprising:
(a) a polymer or monomer, wherein said polymer or monomer has a non-leachable radio-opaque moiety, and
(b) a polyvinylpyrrolidone-polyurethane complex, wherein said polymer is a natural polymer or a synthetic polymer or a combination thereof; wherein said synthetic polymer is a polymer blend, alloy, random copolymer, block copolymer, graft copolymer or homopolymer; wherein said synthetic polymer comprises poly(vinyl alcohol), poly(vinylpyrrolidone), poly(caprolactone), poly(hydroxybutarates), poly(caprolactams), poly(terephthalate), poly(vinyl chloride), poly(propylene), poly(ethylene oxide), poly(propylene oxide), poly(styrene), poly(ethylene), poly(urethanes), silicone elastomers or combinations thereof; wherein said monomer is an allyllic compound, amide, amine, anhydride, epoxide, isocyanate, silyl, thiol compound, thioisocyanate, vinyl compound, ester, acid chloride, acrolein or acryloylchoride; and wherein said polymer or said monomer has at least one reactive functional group, wherein said reactive functional group is an isocyanate, an isothiocyanate, an epoxide, a carboxylic ester, a tresylate, an anhydride or a carboxylic acid; and wherein said non-leachable radio-opaque moiety is covalently attached to said polymer or said monomer.

37. An object covered with a primer comprising: wherein said primer comprises a monomer, wherein said monomer has a non-leachable radio-opaque moiety, wherein said monomer has at least one reactive functional group, wherein said reactive functional group is an isocyanate, an isothiocyanate, an ester, an aldehyde, an N-hydroxysuccinimide ester, an epoxide, a carboxylic ester, a tresylate, an anhydride, an alkyl halide, a carboxylic acid, a haloketone, an alkene, an alkyne or an acyl chloride; and wherein said monomer is covalently attached to said object by a covalent linkage.

38. An object covered with a primer comprising: wherein said primer comprises a monomer and a polyvinylpyrrolidone-polyurethane complex; wherein said monomer has a non-leachable radio-opaque moiety, wherein said monomer has at least one reactive functional group, wherein said reactive functional group is an isocyanate, an isothiocyanate, an ester, an aldehyde, an N-hydroxysuccinimide ester, an epoxide, a carboxylic ester, a tresylate, an anhydride, an alkyl halide, a carboxylic acid, a haloketone, an alkene, an alkyne or an acyl chloride; and wherein said monomer adheres to said object.

39. A radio-opaque covering composition comprising:

(a) a polymer or monomer, wherein said polymer or monomer has a non-leachable radio-opaque moiety, and (b) an aqueous coating solution comprising a blend of a polyacrylate and a poly(ethylene oxide), wherein said polymer is a natural polymer or a synthetic polymer or a combination thereof; wherein said synthetic polymer is a polymer blend, alloy, random copolymer, block copolymer, graft copolymer or homopolymer; wherein said synthetic polymer comprises poly(vinyl alcohol), poly(vinylpyrrolidone), poly(caprolactone), poly(hydroxybutarates), poly(caprolactams), poly(terephthalate), poly(vinyl chloride), poly(propylene), poly(ethylene oxide), poly(propylene oxide), poly(styrene), poly(ethylene), poly(urethanes), silicone elastomers or combinations thereof; wherein said monomer is an allyllic compound, amide, amine, anhydride, epoxide, isocyanate, silyl, thiol compound, thioisocyanate, vinyl compound, ester, acid chloride, acrolein or acryloylchoride; and wherein said polymer or said monomer has at least one reactive functional group, wherein said reactive fuinctional group is an isocyanate, an isothiocyanate, an epoxide, a carboxylic ester, a tresylate, an anhydride or a carboxylic acid; wherein said non-leachable radio-opaque moiety is covalently attached to said polymer or said monomer.

40. A radio-opaque covering composition comprising:

a) a polymer or monomer, wherein said polymer or monomer has a non-leachable radio-opaque moiety, and (b) a block copolymer of a dimethylacrylamide and glycidyl methacrylate, wherein said polymer is a natural polymer or a synthetic polymer or a combination thereof; wherein said synthetic polymer is a polymer blend, alloy, random copolymer, block copolymer, graft copolymer or homopolymer; wherein said synthetic polymer comprises poly(vinyl alcohol), poly(vinylpyrrolidone), poly(caprolactone), poly(hydroxybutarates), poly(caprolactams), poly(terephthalate), poly(vinyl chloride), poly(propylene), poly(ethylene oxide), poly(propylene oxide), poly(styrene), poly(ethylene), poly(urethanes), silicone elastomers or combinations thereof; wherein said monomer is an allyllic compound, amide, amine, anhydride, epoxide, isocyanate, silyl, thiol compound, thioisocyanate, vinyl compound, ester, acid chloride, acrolein or acryloylchoride; and wherein said polymer or said monomer has at least one reactive functional group, wherein said reactive functional group is an isocyanate, an isothiocyanate, an epoxide, a carboxylic ester, a tresylate, an anhydride or a carboxylic acid; wherein said non-leachable radio-opaque moiety is covalently attached to said polymer or said monomer.

* * * * *

UNITED STATES PATENT AND TRADEMARK OFFICE
CERTIFICATE OF CORRECTION

PATENT NO.    : 6,599,448 B1　　　　　　　　　　　　　　　　　　　　　　　　Page 1 of 1
DATED         : July 29, 2003
INVENTOR(S)   : Ehrhard, Jr. et al.

It is certified that error appears in the above-identified patent and that said Letters Patent is hereby corrected as shown below:

Column 2,
Line 2, reads "lodochlorhydroxyquin," should read -- Iodochlorhydroxyquin, --;

Column 15,
Line 59, reads "according to claim 2" should read -- according to claim 5 --; and Column 18,
Line 38, reads "and a a polyvinylpyrrolidone-polyurethane" should read
-- and a polyvinylpyrrolidone-polyurethane --

Signed and Sealed this

Twenty-eighth Day of October, 2003

JAMES E. ROGAN
*Director of the United States Patent and Trademark Office*